United States Patent
Alaluf et al.

(10) Patent No.: US 6,287,553 B1
(45) Date of Patent: Sep. 11, 2001

(54) SKIN CARE COMPOSITION

(75) Inventors: Simon Alaluf; Martin Richard Green; Clive Roderick Harding, all of Bedford; Heng-Long Hu, Gloucester, all of (GB); Gerald Patrick McNeill, Channahon, IL (US); Jonathan Richard Powell, Bedford (GB); Anthony Vincent Rawlings, Wirral (GB); Julia Sarah Rogers; Allan Watkinson, both of Bedford (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/459,698

(22) Filed: Dec. 13, 1999

(30) Foreign Application Priority Data

Dec. 22, 1998 (GB) ................................ 9828379

(51) Int. Cl.$^7$ .................................... A61K 31/74
(52) U.S. Cl. ....................... 424/78.03; 424/400; 424/401; 424/489; 424/59; 514/844; 514/845; 514/846; 514/847; 514/848
(58) Field of Search ..................................... 424/401, 489, 424/78.03, 59; 514/844–848

(56) References Cited

U.S. PATENT DOCUMENTS

| 4,393,043 | 7/1983 | Koulbanis et al. ................... 424/59 |
| 6,019,990 | * 2/2000 | Remmereit ........................... 424/401 |

FOREIGN PATENT DOCUMENTS

97/18320   5/1997  (WO) .

* cited by examiner

*Primary Examiner*—Thurman K. Page
*Assistant Examiner*—Charesse L. Evans
(74) *Attorney, Agent, or Firm*—Milton L. Honig

(57) ABSTRACT

A topical composition and cosmetic method for treating skin conditions selected form the group consisting of wrinkling, sagging, photodamaged skin, sensitive skin, dry skin, flaky skin, red skin, irritated skin, itchy skin and age spots, the composition comprising:

(a) conjugated linoleic acid, and/or derivatives thereof comprising conjugated linoleic acid moieties, in which at least 50% by weight of the conjugated linoleic acid and/or moieties, is present as the cis 9 trans 11 isomer; and
(b) a dermatologically acceptable carrier.

4 Claims, No Drawings

SKIN CARE COMPOSITION

FIELD OF THE INVENTION

This invention relates to topical compositions for application to human skin and to their use in improving the condition and appearance of skin.

BACKGROUND AND PRIOR ART

Skin is subject to deterioration through dermatological disorders, environmental abuse (wind, air conditioning, central heating) or through the normal aging process (chronoaging) which may be accelerated by exposure of skin to sun (photoaging). In recent years the demand for cosmetic compositions and cosmetic methods for improving the appearance and condition of skin has grown enormously.

Consumers are increasingly seeking "anti-aging" cosmetic products which treat or delay the visible signs of chronoaging and photoaging skin such as wrinkles, lines, sagging, hyperpigmentation and age spots.

Consumers also frequently seek other benefits from cosmetic products in addition to anti-aging. The concept of "sensitive skin" has also raised the consumer demand for cosmetic products which improve the appearance and condition of sensitive, dry, rough and/or flaky skin and to soothe red, irritated and/or itchy skin. Consumers also desire cosmetic products which treat spots, pimples, blemishes etc.

Skin care cosmetic and dermatological compositions for improving the condition and appearance of skin comprising long chain triglyceride esters of polyunsaturated essential fatty acids, the free acids and their alkali or ammonium salts are well known in the art. For instance, GB 2181349 A describes inter alia a composition composed of triglycerides of linoleic acid for improving the smoothness and elasticity of skin. A commercial product, "Linola Fett n" ex Dr. August Wolff Gmbh, is available for the treatment of dry skin diseases, and dermatoses, which contains inter alia a mixture of the 9,11 isomers of conjugated linoleic acid.

There continues to be a need, however, for alternative effective cosmetic compositions for topical application to skin for treating/delaying the visible signs of aging and photodamaged skin such as wrinkles, lines, sagging, hyperpigmentation and age spots. Compositions and cosmetic methods which provide other skin care benefits in addition to anti-aging such as for improving the appearance and condition of dry, rough and flaky skin and to soothe irritated and itchy skin are particularly desirable.

We have now surprisingly found that effective treatment and prevention of normal skin conditions due to chronoaging or photoaging, such as wrinkles, lines, sagging, hyperpigmentation and age spots, and/or of sensitive, dry, rough, flaky, red, itchy, irritated skin may be obtained through the application of cosmetic compositions to the skin which are specifically enriched in a particular isomer of conjugated linoleic acid or derivatives thereof.

SUMMARY OF THE INVENTION

According to a first aspect of the present invention there is provided a topical composition comprising:
(a) conjugated linoleic acid, and/or derivatives thereof comprising conjugated linoleic acid moieties, in which at least 50% by weight of the conjugated linoleic acid and/or moieties is present as the cis 9 trans 11 isomer; and
(b) a dermatologically acceptable vehicle.

Such compositions are particularly useful for topical application to human skin for cosmetically treating/preventing skin conditions selected from the group consisting of wrinkling, sagging, photodamaged skin, sensitive skin, dry skin, rough skin, flaky skin, red skin, irritated skin, itchy skin and age spots. The compositions are also useful for application to the skin as a cosmetic treatment for spots, pimples and blemishes or as a cosmetic skin care product which promotes dermal repair and/or boosts collagen deposition in skin.

According to a second aspect the present invention provides a cosmetic method of treating/preventing skin conditions selected from the group consisting of wrinkling, sagging, photodamaged skin, sensitive skin, dry skin, rough skin, flaky skin, red skin, irritated skin, itchy skin and age spots, the method comprising applying to the skin a topical composition as described above.

In a further aspect, the invention also provides the use of conjugated linoleic acid, and/or derivatives thereof comprising conjugated linoleic acid moieties, in a topical composition for treating/preventing skin conditions selected from the group consisting of wrinkling, sagging, photodamaged skin, dry skin, rough skin, flaky skin, sensitive skin, irritated skin, itchy skin and age spots, wherein at least 50% by weight of the conjugated linoleic acid and/or moieties is present as the cis 9 trans 11 isomer.

The inventive compositions and methods thus provide anti-aging benefits which result in the promotion of smooth and supple skin with improved elasticity and a reduced or delayed appearance of wrinkles and aged skin with improved skin colour. A general improvement in the appearance, texture and condition, in particular with respect to the radiance, clarity, and general youthful appearance of skin is achieved. The inventive compositions and methods are also beneficial for soothing and calming sensitive, dry, rough, irritated, red, flaky and itchy skin. Thus the inventive methods and compositions advantageously provide a wide range of skin care benefits.

The term "treating" as used herein includes within its scope reducing, delaying and/or preventing the above mentioned skin conditions such as wrinkled, aged, photodamaged, dry and/or irritated skin and generally enhancing the quality of skin and improving its appearance and texture by preventing or reducing wrinkling and increasing flexibility, firmness, smoothness, suppleness and elasticity of the skin. The cosmetic compositions, methods and the uses of the conjugated linoleic acid according to the invention may be useful for treating skin which is already in a wrinkled, aged, photodamaged, dry and irritated condition or for treating youthful skin to prevent or reduce those aforementioned deteriorative changes due to the normal aging/photo aging process.

DETAILED DESCRIPTION OF THE INVENTION

Cis 9,trans 11 Isomer Enriched Conjugated Linoleic Acid

Conjugated linoleic acid (hereinafter referred to as CLA) comprises a group of positional and geometric isomers of linoleic acid in which various configurations of cis and trans double bonds at positions (6, 8), (7, 9), (8, 10), (9, 11), (10, 12) or (11, 13) are possible. Thus twenty-four different isomers of CLA exist.

The essential active of the compositions in accordance with the present invention is the c9, trans 11 (hereinafter referred to as c9, t11) isomer. This particular isomer of the free acid has the structure (I) shown below:

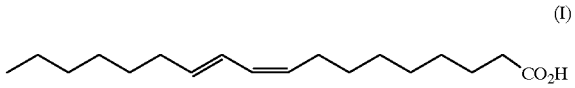

(I)

The invention also includes derivatives of the free acid which thus comprise conjugated linoleic acid moieties. Preferable derivatives include those derived from substitution of the carboxyl group of the acid, such as esters (eg retinyl esters, triglyceride esters, monoglyceride esters, diglyceride esters, phosphoesters), amides (eg ceramide derivatives), salts (eg alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of CLA substituents on the glycerol backbone are included. The triglycerides must contain at least one CLA moiety. For example, of the three esterifiable positions on the glycerol backbone, the 1 and 2 positions may be esterified with CLA and by another lipid at position 3 or as an alternative, the glycerol backbone could be esterified by CLA at the 1 and 3 positions with another lipid at position 2.

Wherever the term "conjugated linoleic acid" or "CLA" is used in this specification it is to be understood that the derivatives thereof comprising CLA moieties are also included. "CLA moieties" refers to CLA fatty acyl portion(s) of a CLA derivative.

By "c9 t11 isomer enriched CLA" is meant that at least 50% by weight of the total CLA (and/or CLA) moieties present in the composition is in the form of the cis 9, trans 11 isomer. Preferably, at least 70%, most preferably at least 90%, by weight of the total CLA and/or CLA moieties present in the composition, is in the form of the c9, t11 isomer.

The CLA and/or derivatives thereof comprising CLA moieties according to the present invention (in which at least 50% by weight of the total CLA and/or CLA moieties present in the composition is in the form of the cis 9, trans 11 isomer) may be prepared according to the method disclosed in WO 97/18320. A preferred method of preparation is disclosed in Example 1 below.

The active, c9 t11 isomer enriched CLA, to be employed in accordance with the present invention is present in the topical composition in an effective amount. Normally the total amount of the active is present in an amount between 0.00001% and 50% by weight of the composition. More preferably the amount is from 0.01% to 10% and most preferably from 0.1% to 5% in order to maximise benefits at a minimum cost.

Dermatologically Acceptable Vehicle

The composition according to the invention also comprises a dermatologically/cosmetically acceptable vehicle to act as a dilutant, dispersant or carrier for the active, c9 t11 isomer enriched CLA. The vehicle may comprise materials commonly employed in skin care products such as water, liquid or solid emollients, silicone oils, emulsifiers, solvents, humectants, thickeners, powders, propellants and the like.

The vehicle will usually form from 5% to 99.9%, preferably from 25% to 80% by weight of the composition, and can, in the absence of other cosmetic adjuncts, form the balance of the composition.

Optional Skin Benefit Materials and Cosmetic Adjuncts

Besides the active, c9 t11 isomer enriched CLA, other specific skin-benefit actives such as sunscreens, skin lightening agents, skin tanning agents may also be included.

The vehicle may also further include adjuncts such as perfumes, anti-oxidants, opacifiers, preservatives, colourants and buffers.

Product Preparation, Form, Use and Packaging

To prepare the topical composition according to the present invention the usual manner for preparing skin care products may be employed. The active components are generally incorporated in a dermatologically acceptable carrier in conventional manner. The active components can suitably first be dissolved or dispersed in a portion of the water or another solvent or liquid to be incorporated in the composition. The preferred compositions are oil-in-water or water-in-oil emulsions.

The composition may be in the form of conventional skin-care products such as a cream, gel or lotion or the like. The composition can also be in the form of a so-called "wash-off" product eg a bath or shower gel, possibly containing a delivery system for the actives to promote adherence to the skin during rinsing. Most preferably the product is a "leave-on" product; a product to be applied to the skin without a deliberate rinsing step soon after its application to the skin.

The composition may packaged in any suitable manner such as in a jar, a bottle, tube, roll-ball, or the like, in the conventional manner.

The method of the present invention may be carried out one or more times daily to the skin which requires treatment. The improvement in skin appearance will usually become visible after 3 to 6 months, depending on skin condition, the concentration of the active components used in the inventive method, the amount of composition used and the frequency with which it is applied. In general, a small quantity of the composition, for example from 0.1 to 5 ml is applied to the skin from a suitable container or applicator and spread over and/or rubbed into the skin using the hands or fingers or a suitable device. A rinsing step may optionally follow depending on whether the composition is formulated as a "leave-on" or a "rinse-off" product.

In order that the present invention may be more readily understood, the following examples are given, by way of illustration only.

EXAMPLES

Example 1

This example illustrates synthesis of CLA comprising (1) a mixture of c9, t11 isomer and t10, c12 isomer in a 1:1 ratio; (2) 93% c9 t11 isomer by weight of total CLA moieties, a compound included in the inventive compositions; and (3) 80.5% t10 c12 isomer by weight of total CLA moieties, a compound outside the scope of the present invention.

Mixed isomers of CLA are prepared by high temperature alkali treatment of Safflower oil, generating CLA with equal amounts of the c9,t11 and t10,c12 CLA isomers. CLA enriched in the c9,t11 CLA is separated from the mix by selective esterificaton with lauryl alcohol using *Geotrichum Candidum* as a catalyst. The enriched c9t11 CLA is hydrolysed and converted to the triglyceride. After the esterification step and separation the remaining CLA free acids are enriched in t10,c12 CLA.

1. Production of Mixed Isomers of CLA

'Analar Reagent' (AR) sodium hydroxide (0.6 kg) was dissolved in 6 kg of pharmaceutical grade propylene glycol by mixing and heating to 80–85° C. The sample was cooled and 2 kg of safflower oil was added. Using standard pilot scale equipment the mixture was refluxed for 3 hours with fast stirring at 170° C. The reaction mix was cooled to about 95° C., the stirrer reduced to an intermediate speed, and the mix neutralised using 1.280 liter of 35.5% hydrochloric acid dissolved in demineralised water (8 liters), keeping the temperature at about 90° C. The reaction mix was allowed to settle and the aqueous phase was run off. The oil phase was washed with 2×1 liter of 5% AR salt solution and by 2×1 liter of demineralised water at 90° C., discarding any soapy material. The CLA enriched oil was dried at 100° C. under vacuum before draining at about 50° C. and filtered through a buchner system containing a Whatman filter and a thin layer of celite-hyflo-filter aid. The mixed isomer CLA oil was stored under nitrogen at −25° C. until required. The composition of the oil produced by this method is set out in table 1 below:

TABLE 1

| Composition of mixed CLA fatty acids (wt %): | Relative Percentage of Total fatty acid lipid |
|---|---|
| c9,t11 | 34.1 (47% of total CLA) |
| t10,c12 | 34.1 (47% of total CLA) |
| c9,c11 & c10,c12 | 2.3 |
| t9,t11t & t10,12t | 0.7 |
| Other CLA | 1.4 |
| Total CLA | 72.6 |
| 16:0 | 7.0 |
| 16:1 | 0.8 |
| 18:0 | 2.5 |
| 18:1 | 13.3 |
| 18:2 (non-CLA) | 3.3 |
| Other fatty acid | 0.5 |

2. Production of c9 t11 Isomer Enriched CLA (I) Preparation of Lauryl Esters:

CLA prepared from Safflower (2.0 kg) was added to 2×molar equivalents of lauryl alcohol (1-dodecanol; 98% ex Aldrich chemicals) along with 5.96 kg of demineralised water. The temperature was adjusted to 25° C. and 1% (w/w) of *Geotrichum Candidum* (ex Amano Pharmaceuticals, Japan) was added premixed with a little water, and mixed vigorously. The reaction was stopped at 44 hours. The vessel was heated to 80–90° C., the aqueous layer drained and the oil was washed with demineralised water and dried at 100° C. under vacuum for 30 minutes. The oil was cooled to 50° C. and filtered through a buchner system containing a Whatman filter and a thin layer of celite-hyflo-filter aid.

(II) Separation of the Enriched c9,t11 CLA Esters:

Residual lauryl alcohol was removed at 130° C. at 25–35 ml per minute by molecular distillation. The residue was coarsely separated into the lauryl esters (enriched in c9,t11 CLA) and free acids (enriched in t10,c12 CLA) by evaporation at 158° C. at a flow rate of 25–35 ml per minute. Any remaining free acids in the lauryl ester residue was reduced by a further distillation at 171° C. at a flow rate of 30–40 ml per minute. 2790 g of lauryl ester residue was neutralised at 90° C. using 330 ml of 4M AR sodium hydroxide, followed by separation of the oil from the aqueous phase, 3×washes of the oil in demineralised hot water, a further 0.1M alkali wash and two hot water washes. The enriched lauryl ester oil sample was dried as before.

(III) Saponification of the Enriched c9,t11 CLA Lauryl Esters:

Lauryl esters of c9,t11 enriched CLA were saponified using AR sodium hydroxide/96% food grade ethanol and re-acidified using AR concentrated hydrochloric acid. The reaction mix containing the enriched CLA free fatty acids was dried at 100° C. and filtered as before at about 50° C. Lauryl alcohol was evaporated off at 132° C. at 25–30 ml per minute. In order to remove any residual lauryl alcohol, free alcohols were esterified to the fatty acids present in the reaction mix, using SP392 Mucor miehei lipase (5%, batch lux 0110 ex Novo Nordisk). The enriched C9 t11 CLA containing fatty acids were separated from the lauryl esters using molecular distillation under vacuum at 155° C. at 15–20 ml per minute.

The composition of the enriched C9 t11 CLA produced by the above method is set out in table 2 below:

TABLE 2

| Composition of typical preparation of enriched c9,t11 CLA fatty acids (wt %): | Relative Percentage of Total Fatty Acid Lipid |
|---|---|
| c9,t11 | 66.1 (93% of total CLA) |
| t10,c12 | 4.1 |
| c9,c11 & c10,c12 | 0.3 |
| t9,t11t & t10,12t | 0.4 |
| Other CLA | 0.2 |
| Total CLA | 71.1 |
| 16:0 | 1.6 |
| 16:1 | — |
| 18:0 | 0.4 |
| 18:1 | 22.3 |
| 18:2 (non-CLA) | 4.5 |
| Other fatty acid | 0.1 |

3. Isolation of the t10,c12 Isomer Enriched CLA

The CLA free acids from step (II) above were distilled again at 160–165° C. and 20–30 ml/min to reduce the ester content. Residual lauryl alcohol was reduced further by a distillation at 131° C. and 25–30 ml/min flow rate. Any remaining lauryl alcohol was reduced by re-esterifiction as described in step (III) above for the c9,t11 isomers, using SP392 Mucor miehei lipase. Any lauryl esters formed were removed by distillation as described for the c9,t11 isomer, generating the enriched t10,c12 CLA, the composition of which is set out in the table 3 below:

TABLE 3

| Composition of typical preparation of enriched t10.c12 CLA fatty acids (wt %): | Relative Percentage of Total Fatty Acid Lipid |
|---|---|
| c9,t11 | 8.3 |
| t10,c12 | 53.9 (80.5% of total CLA) |
| c9,c11 & c10,c12 | 2.9 |
| t9,t11t & t10,12t | 1.1 |
| Other CLA | 0.7 |
| Total CLA | 66.9 |
| 16:0 | 13.6 |
| 16:1 | — |
| 18:0 | 4.6 |
| 18:1 | 10.3 |
| 18:2 (non-CLA) | 3.1 |
| Other fatty acid | 1.5 |

Example 2

Preparation of c9,t11 CLA Triglycerides:

Enriched c9,t11 CLA (55 g) prepared according to example 1 was mixed with 5.55 g (10.1%) of glycerol (Pricerine 9083 glycerine CP from Ellis and Everards) and 3 g (approximately 5%) of SP392 Mucor Meihie non-specific lipase (Mucor Meihie Ex Novo Nordisk Batch Lux 0110) was added. The mixed materials were stirred under vacuum in a rotary-evaporator at 60° C. with a slight nitrogen bleed.

After 24 hours the free fatty acid level reduced to 12.7% and a further 0.15 g of glycerol was added. After 48 hours the free fatty acid level reduced to 3.4% and the reaction was stopped by filtering the mixture through a thin layer of celite super-cel filter aid on a buchner filter collecting the CLA triglyceride oil phase, the composition of which is set out in table 4 below:

TABLE 4

| Fatty Acid composition of the triglycerides | Relative Percentage of Total fatty acid Lipid |
|---|---|
| c9,t11 | 64.9 (93% of CLA) |
| t10,c12 | 3.9 |
| c9,c11 & c10,c12 | 0.4 |
| t9,t11t & t10,12t | 0.6 |
| Other CLA | — |
| Total CLA | 69.8 |
| 16:0 | 1.7 |
| 16:1 | 0.9 |
| 18:0 | 0.5 |
| 18:1 | 22.4 |
| 18:2 (non-CLA) | 4.5 |
| Other fatty acid | 0.2 |

Example 3

This example demonstrates the anti-aging benefits of a c9 t11 isomer enriched CLA.

Identification of Procollagen-I and Decorin Upregulation In Skin In Vivo Following Topical Retinoic Acid Treatment for Comparative Purposes Collagen, the predominant matrix skin protein is known to impart tensile strength to skin. Decorin is a proteoglycan which is known to be important for controlled and correct deposition of collagen in the extracellular matrix of skin. It is also known in the art that the levels of collagen and decorin in skin are significantly reduced with aged and/or photodamaged skin. Many studies have shown that the levels of collagen type I in skin is decreased with age and/or with increased photodamage, (for example Lavker, R. J.Inv.Derm.,(1979),73,79–66; Griffiths et al. N. Eng. J. med. (1993) 329, 530–535). In the case of decorin, it has been shown that mRNA expression and expression of the proteoglycan is greatly reduced in photodamaged skin in vitro (Bernstein et al. Lab. Invest.(1995)72,662–669). The reduction of the levels of these skin proteins is accordingly associated with a decrease in the tensile strength of the skin causing wrinkles and laxity.

It is well known in the art that retinoic acid is a potent anti-aging active and induces dermal repair of photodamaged skin. It has been shown that wrinkle effacement and dermal repair following topical treatment of skin with retinoic acid arises through new collagen deposition and synthesis in the skin (for example, Griffiths et al. N. Eng. J. med. (1993) 329, 530–535). It is widely accepted that strengthening of the dermal matrix by boosting the level of collagen in skin using retinoic acid provides anti-aging/dermal repair benefits. Procollagen I is a precursor of collagen. Increased production of procollagen I in response to a test compound application is a marker of an increased collagen level.

Two groups of women were recruited with identical or nearly identical degrees of mild to moderate photodamage on each outer forearm. They were supplied with 0.05% retinoic acid in a moisturising base (Retinova®) and also with a colour matched moisturising cream with similar sensory characteristics (Dermacare® lotion) but no active ingredients as a placebo control. Each participant of the two groups applied the Retinova® to one outer forearm and placebo (Dermacare®) to the other outer forearm. Group 1 applied the products daily to their outer forearms for 14 weeks and the Group 2 applied the products to their outer forearms for 28 weeks. At the end of the studies two full thickness 4 mm punch biopsies were taken from the treated areas of each forearm. Immunohistochemical analysis of the biopsy tissue taken from the participants was performed to identify the effect of retinoic acid treatment on the expression of the skin extracellular matrix components decorin and procollagen-I as compared with the placebo treated forearms. The following procedure was followed:

Materials

Antibody dilution buffer for wax sections was composed of Tris Buffered Saline (TBS), 3% bovine serum albumin (BSA), 0.05% Triton X-100 and 0.05% sodium azide. Primary antibodies for procollagen-I (amino terminal) were obtained from Chemicon International Inc. (cat# MAB 1912, rat IgG1) and used on wax sections at a dilution of 1:800, overnight at 4° C. after the section had been pre-treated trypsin (0.5 mg/ml, 25 minutes, 37° C.). Primary antibodies for decorin were obtained from Biogenesis (rabbit polyclonal) and used on wax sections at a dilution of 1:800, overnight at 4° C. Anti-rat biotinylated secondary antibodies were obtained from DAKO (cat# E0468, rabbit polyclonal) was applied to wax sections at a dilution of 1:400. Anti-rabbit biotinylated secondary antibodies were obtained from Amersham (cat# RPN 1004, donkey polyclonal) was applied to wax sections at a dilution of 1:400. Streptavidin conjugated alkaline phosphatase was obtained from Zymed (cat# 43-4322) and used at a concentration of 1:2500. Fast Red chromogen was obtained from DAKO (cat# K597). Gills #3 Haemotoxylin nuclear counterstain was obtained from Sigma (cat# GHS-3), filtered and used without dilution. Trypsin was obtained from Sigma (cat# T-7186) and slides were mounted with Glycergel from DAKO (cat# C563). METHODS Wax sections of the biopsy tissue were mounted on silane coated slides and baked for 18 hours at 55° C. The slides were dewaxed through xylene and alcohol and brought to water and then transferred to TBS. DAKO® pen was used to ring the sections. The sections were processed for antigen retrieval using trypsin where necessary, as indicated for each antibody. Where antigen retrieval was necessary, the slides were incubated for 25 minutes at 35° C. with trypsin at 0.5 mg/ml (Sigma Cat # T-7186). The protease was subsequently rinsed off (2×2 minutes) with TBS. Following antigen retrieval, if necessary, or otherwise directly after ringing the sections, non specific antibody binding was blocked with 5% solutions of secondary antibody host serum in TBS/0.5% BSA/0.1% sodium azide as the blocking solution for at least 20 mins at room temperature in a humid chamber. The excess blocking solution was drained off, but the sections were not allowed to dry. The sections were then incubated with the primary antibody (appropriately diluted as indicated above) in a humid chamber overnight at 4° C. Antibody was subsequently drained from the sections, without allowing them to dry. The slides were then washed with TBS to remove unbound primary antibody—a one minute rinse followed by three five minute washes—and then incubated with the appropriate secondary antibody (appropriately diluted as indicated above) in a humid chamber for 1 hour at room temperature. The antibody solution was subsequently drained from the slides without allowing the section to dry. The slides were washed in TBS, a one minute rinse followed by 4×5 min washes, in order to remove the unbound secondary antibody. For the biotinylated secondary antibody the sections were subsequently incubated with streptavidin conjugate for 45 mins at 37° C. and then washed in TBS to remove unbound streptavidin conjugate. The chromogen was added and the colour developed with observation to avoid over-staining. The sections were then counterstained and mounted.

Differences in the expression of procollagen-I and decorin between retinoic acid (Retinova®) and placebo (Dermacare®) treated sites were determined by visual assessment of the immunohistochemically stained sections using light microscopy.

This analysis identified marked upregulation of both procollagen-I and decorin in the photodamaged skin following topical application of retinoic acid (Retinova®), as set out in Table 5 below.

TABLE 5

Effect of Retinoic Acid Treatment on expression of procollagen I and decorin in skin In Vivo

| | Total No. of Participants | No. of Participants showing marked increase in expression of procollagen-I | No. of Participants showing marked increase in expression of decorin |
| --- | --- | --- | --- |
| Group 1 after 14 weeks | 16 | 9 | 10 |
| Group 2 after 28 weeks | 15 | 10 | 15 |

The extracellular matrix components procollagen 1 and decorin are thus clearly identifiable markers of retinoic acid induced dermal repair.

Procedure For Measuring Decorin Synthesis In Human Dermal Fibroblasts

Preparation of Dermal Fibroblast Conditioned Medium

Primary human foreskin fibroblasts at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents and vehicle controls were added to the cells in triplicate in a final volume of 0.4 ml/well fresh serum free DMEM and incubated for a further 24 hours. This fibroblast conditioned medium was either analysed immediately or snap frozen in liquid nitrogen and stored at −70° C. for future analysis. The cells were then counted and data from the dot-blot analysis subsequently standardised to cell number.

Dot Blot Assay for Decorin Protein in Dermal Fibroblast Conditioned Medium

Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm$^2$ in a 175 cm$^2$ flask and maintained in serum free DMEM as described above. Assay samples were subsequently applied in triplicate to a prewetted sheet of Immobilon-P transfer membrane using the 96-well Bio-Dot Apparatus from Bio-Rad as described in the manufacturers guidelines. Approximately 200 µl of medium was applied per well. The medium was allowed to filter through the membrane under gravity (30 minutes) after which the membrane was washed twice with PBS (200 µl). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for decorin analysis were blocked with 3% (w/v) BSA/0.1% (v/v) Tween 20 in PBS. The following day, the membranes were probed with 1:10000 dilution of primary antibodies to human decorin (rabbit polyclonal; Biogenesis) for 2 hours at room temperature. The membranes were subsequently washed with TBS/0.05% Tween 20 (3×5 minutes) and then incubated with 1:1000 dilution of anti-rabbit F (ab') 2 fragments (Amersham) for 1 hour at room temperature. Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents on decorin synthesis were determined relative to a vehicle treated control value of 100 arbitrary units.

Tests

The table 6 below indicates the agents that were evaluated for their effects on decorin synthesis in human dermal fibroblasts, and the amounts in which they were applied. In order to normalise the results the effects of the test substances were determined relative to a vehicle treated control value of 100 arbitrary units.

"CLA c9,t11" in the table refers to CLA in which 93% by weight of the total CLA is the c9,t11 isomer i.e. an active agent that is within the scope of the present invention. This was prepared was described in example 1 above.

"CLA t10, c12" in the table refers to CLA in which 80.5% by weight of the total CLA is the t10, c12 isomer having the structure 2 below:

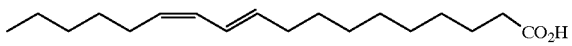

This agent is thus outside the scope of the present invention. It was prepared as described in example 1.

"CLA mixture" in the table refers to a mixture of the c9, t11 isomer and the t10, c12 isomer in a 1:1 ratio, in which 47% of each isomer, by weight of the total CLA, is present. This agent is thus outside the scope of the invention. It was prepared as described in example 1.

The trials performed with "CLA t10,c12" and "CLA mixture" were run for comparative purposes.

Also for comparison, a trial was performed with retinoic acid to assess its effect on decorin synthesis in human dermal fibroblasts. The concentrations of reagents used in the trials had no influence on cell viability.

TABLE 6

The Effect on Decorin Synthesis by Fibroblasts in Response to Treatment with Various Tests Compounds

| Treatment | Decorin |
| --- | --- |
| Control (Vehicle) | 100 |
| CLA, c9,t11 (10 µM) | 151.6 ± 22.4 (p = 0.01, n = 3) |
| CLA Mixture (10 µM) | 81.5 ± 4.3 |
| CLA t10, c12 (10 µM) | 99.3 ± 24.8 |

The results in table 6 indicate that the c9, t11 isomer enriched CLA significantly upregulates the synthesis of decorin in human dermal fibroblasts as compared to the control and as compared to the t10, c12 CLA and the CLA.

The level of decorin in skin is associated with improved condition and appearance of skin. Increasing the level of decorin in skin is important for controlled and correct deposition of collagen in skin which is associated with many skin benefits such as wrinkle effacement and dermal repair of photodamaged skin.

The comparative trial with retinoic acid (1 µm) showed an upregulation of decorin, 138±14.0 (p=0.035, n=4), as determined relative to a vehicle treated control value of 100 arbitrary units. Surprisingly, the data thus further indicates that the magnitude of the upregulation of decorin synthesis in human dermal fibroblasts effected by the c9, t11 isomer of conjugated linoleic acid exceeds that of the bench-mark anti-aging dermal repair active, retinoic acid.

Example 4

This example measures the effect of various test compounds on the keratinocyte toxicity of sodium dodecyl sulphate (SDS).

Keratinocyte SDS Viability Assay

Methodology

Keratinocytes were grown in 96 well plates to approximately 80% confluency in keratinocyte growth medium (KGM) which was then replaced with KGM without hydrocortisone for 24–48 hours. The cells were then treated with a concentration of sodium dodecyl sulphate (SDS) which will produce cell viability of approximately 50% (5µ/ml). The cells were then dosed with test compounds which were used at a concentration indicated in table 3 below. The test compounds "c9 t11 CLA" and "t10 c12 CLA" in table 7 are the same as the agents described above in Example 3. The control did not contain any test compounds. After incubating for 24 hours the medium was removed and the viability determined by the Neutral Red method. With this method the cells were incubated for 3 hours in KGM containing 25 µg/ml neutral red after which the medium was removed and the cells were then extracted with 1 ml of 1% (v/v) acetic acid, 50% (v/v) ethanol for 30 min units. The absorbance of the extract at 562 nm was determined and the viability evaluated by reference to wells which contained neither SDS nor test compounds. The results that were obtained are summarised in table 7 below:

TABLE 7

| Test Compound (concentration) | % of SDS control mean | sd | n |
| --- | --- | --- | --- |
| SDS 5 µg/ml CONTROL | 100.0 | 16.6 | 8 |
| 50 µM CLA c9 t11 + SDS 5 µg/ml | 134.8 | 27.2 | 8 |
| 50 µM CLA t10 c12 + SDS 5 µg/ml | 69.2 | 16.3 | 8 |

The results are expressed as a% of the 5 µg/ml SDS viability value.

The c9 t11 CLA (an agent within the scope of the present invention) significantly increased viability compared to the 5 µg/ml SDS value as determined by 1 way ANOVA with Student-Neumann-Kuels multiple comparison, p<0.05. The t10 c12 CLA (an agent outside the scope of the present invention) did not elevate cell viability compared to the SDS control.

This methodology has shown that the keratinocyte toxicity of an irritant relates to the irritancy effect of the agent in vivo (Lawrence, JN, Starkey, S., Dickson, FM & Benford, DJ. Use of human and rat keratinocyte cultures to assess skin irritation potential. Toxicol. In Vitro. 10, 331–340 (1996).) Thus here we show that treatment with "c9 t11 CLA" significantly reduces the toxic effects of SDS on keratinocytes and accordingly that it has an anti-irritant functionality whereas the "t10 c12 CLA" did not significantly alter the toxicity of SDS on these cells and thus does not have an anti-irritant effect.

Example 5

This example illustrates the ability of the test compounds to induce differentiation in keratinocytes, the differentiation being part of the process which is fundamental to the formation of a mature stratum corneum. A mature stratum corneum is important for the barrier function of skin and helps to prevent skin becoming dry and rough. Cornified envelope (CE) formation and the activity of the transglutaminase enzyme were measured as indicators of differentiation. The cornified envelope is responsible for the shape, strength and structural integrity of the corneocytes within the stratum corneum, and transglutaminase enzyme is vital for the correct formation of the cornified envelope.

Keratinocyte Differentiation Assay

Methodologies

Cell Culture

Human epidermis was isolated from juvenile foreskins using conventional techniques and grown in serum-free keratinocyte growth medium ("KGM"; Clonetics). Third passage keratinocytes, seeded at 4000 cells/well in 96 well plates (Costar) were used in all studies. Keratinocytes were grown for 3 days at 37° C. prior to treatment in KGM containing 30 uM $Ca^{2+}$. Cells were treated with either test compounds or vehicle alone (dimethyl sulphoxide) for 48 hours prior to harvest. The test compounds "c9 t11 CLA" and "t10 c12 CLA" in table 8 are the same as the agents described above in Example 3.

Dna Quantification.

Following treatment cells were washed 3× in phosphate buffered saline (PBS) and then extracted in 100 ul of Triton X-100, 50 mM Tris/HCl pH 8.0 containing 20 uM pepstatin and 20 uM leupeptin. (DNA extraction buffer) 15 ul of this extract was assayed for DNA content using the Pico Green assay (Molecular Probes, 4849 Pichford Avenue, Eugene, Oreg., USA) exactly as described by the manufacturers.

Particulate Transglutaminase (tgase) Activity.

Following treatment with DNA extraction buffer, the cells were washed briefly in fresh buffer and then incubated with the fluorescent tgase substrate Texas Red cadaverine (Molecular Probes). Cells were treated for 16 hours at 37° C. in 15 uM Texas red cadaverine in 50 mM Tris/HCl pH 8.0, 150 mM NaCl containing 5 mM Dithiothreitol, 50 mM $CaCl_2$, washed 2× in distilled water and the fluorescence was measured using a Cytofluor fluorimeter with excitation at 590 nm and emission at 645 nm.

Tgase activity was expressed as fluorescent units/ng of DNA.

Cornified Envelope Formation.

Cornified envelope (CE) formation was assessed by quantitating the SDS insoluble protein remaining in the wells of 24 well plate keratinocyte cultures. After removal of the Triton extraction buffer (described above) the wells were washed with carbonate/bicarbonate buffer (Sigma) pH 9.6. Each well was then incubated with N-hydroxy succinamide coupled to biotin (stock dissolved at 10 mg/ml in DMSO) in the carbonate bicarbonate buffer at 0.1 mg/ml (200 ul/well). The plates were incubated with agitation for 60 minutes at room temperature. 50 ul/well of 10% SDS, 100 mM DTT were added and the plates incubated at 60° C. for a further 60 minutes. The envelopes were filtered (with washing in TBS-Tween)) onto PVDF membrane (pre-blocked in TBS 0.5% Tween) using a dot blot apparatus. The membrane was carefully probed with streptavidin-HRP (Zymed) diluted ¹/₁₀₀₀ for 60 minutes at room temp, washed (TBS-Tween) and incubated with ECL substrate (Pierce) for 2 minutes. The membranes were wrapped in "cling-film" and exposed to X-ray film to visualise the protein. The spot intensity was quantitated by scanning and Phoretix analysis. The results are summarised in table 8 below. The results are expressed as a percentage of the control value for each parameter measured.

TABLE 8

| Test Compound (concentration) | Tgase activity (% control) | sd | n | CE formation (% control) | sd | n |
|---|---|---|---|---|---|---|
| CONTROL | 100.0 | 15 | 6 | 100 | 30 | 6 |
| 10 μM "c9 t11 CLA" | 166* | 20 | 6 | 515* | 28 | 6 |
| 10 μM "t10 c12 CLA" | 101 | 14 | 6 | 107 | 43 | 6 |

*p <0.01

The "c9 t11 CLA" (an agent within the scope of the present invention) significantly (p<0.01) increased transglutaminase activity and CE formation compared to the control (DMSO treated only). The "t10 c12 CLA" (an agent outside the scope of the present invention) did not elevate either of these two parameters of keratinocyte differentiation compared to the control.

Thus we show that treatment with "c9 t11 CLA" significantly increases the differentiation of keratinocytes in vitro and accordingly that it has a differentiation enhancement functionality whereas the "t10 c12 CLA" does not significantly alter the differentiation status of the keratinocytes and thus does not have a differentiation enhancement effect. "c9 t11 CLA" is accordingly useful for the prevention of dry and rough skin conditions and for smoothing and moisturising skin already in a dry and rough condition.

Example 6

The formulation below describes an oil in water cream incorporating the inventive composition which is suitable for the methods and uses according to the present invention. The percentages indicated are by weight of the composition unless stated otherwise.

|  | wt % |
|---|---|
| Mineral Oil | 4 |
| CLA triglyceride (93% c9,t11 isomer by weight of total CLA moieties) made according to Example 2 | 1.15 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

Example 7

The formulation below describes a water in oil emulsion incorporating the inventive composition which is suitable for the methods and cases according to the present invention. The percentages indicated are by weight of the composition unless stated otherwise.

|  | Wt % |
|---|---|
| Fully hydrogenated coconut oil | 9.9 |
| CLA triglyceride (93% C9,t11 isomer by weight of total CLA moieties) made according to Example 2 | 2 |
| Brij 92* | 5 |
| Bentone 38 | 0.5 |
| $MgSO_4 7H_2$ | 0.5 |
| Butylated hydroxytoluene | 0.01 |
| Perfume | qs |
| Water | to 100 |

*Brij 92 is polyoxyethylene (2) oleyl ether

Both the above topical compositions of example 5 and 6 provide an effective cosmetic treatment to improve the appearance of wrinkled, aged, photodamaged, and/or irritated skin, when applied to skin that has deteriorated through the aging or photoaging or when applied to youthful skin to help prevent or delay such deteriorative changes. The compositions can be processed in conventional manner.

What is claimed is:

1. A topical composition comprising:
   (a) conjugated linoleic acid, consisting of conjugated linoleic acid moieties, in which at least 50% by weight of the conjugated linoleic acid and/or moieties is present as the cis 9 trans 11 isomer; and
   (b) a dermatologically acceptable carrier.

2. A composition according to claim 1 comprising 0.00001% to 50%, by weight of the composition of said conjugated linoleic acid and/or derivatives.

3. A cosmetic method of treating and/or preventing skin conditions selected form the group consisting of wrinkling, sagging, photodamaged skin, dry skin, rough skin, flaky skin, irritated skin, itchy skin, sensitive skin and/or age spots, the method comprising applying to the skin a topical composition according to claim 1.

4. A composition according to claim 1 comprising 0.01% to 10% by weight of the composition of said conjugated linoleic acid and/or derivatives.

* * * * *